United States Patent
Vigil et al.

(10) Patent No.: US 6,210,392 B1
(45) Date of Patent: *Apr. 3, 2001

(54) METHOD FOR TREATING A WALL OF A BLOOD VESSEL

(75) Inventors: Dennis M. Vigil, San Diego; Robert E. Reiss, La Jolla, both of CA (US); Peter Barath, Oak Brook, IL (US)

(73) Assignee: Interventional Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,392

(22) Filed: Jan. 15, 1999

(51) Int. Cl.⁷ .................................................. A61M 31/00
(52) U.S. Cl. ...................... 604/507; 604/509; 604/103.02
(58) Field of Search ................... 604/19, 27, 28, 604/48, 500, 501, 507–509, 522, 73, 93, 96, 97, 104, 105, 107

(56) References Cited

U.S. PATENT DOCUMENTS

| | | |
|---|---|---|
| 2,816,552 | 12/1957 | Hoffman . |
| 3,593,713 | 7/1971 | Bogoff et al. . |
| 3,635,223 | 1/1972 | Klieman . |
| 3,993,538 | 11/1976 | Lebowitz et al. . |
| 4,101,646 * | 7/1978 | Sugimoto ................................ 424/4 |
| 4,140,126 | 2/1979 | Choudhury . |
| 4,273,128 | 6/1981 | Lary . |
| 4,318,400 | 3/1982 | Peery et al. . |
| 4,416,865 * | 11/1983 | Rhodes et al. ......................... 924/1.1 |
| 4,441,509 | 4/1984 | Kotsifas et al. . |
| 4,465,072 | 8/1984 | Taheri . |
| 4,922,926 | 5/1990 | Hirschberg . |
| 5,009,659 | 4/1991 | Hamlin et al. . |
| 5,030,201 | 7/1991 | Palestrant . |
| 5,070,877 | 12/1991 | Mohiuddin et al. . |
| 5,100,425 | 3/1992 | Fischell et al. . |
| 5,112,305 * | 5/1992 | Barath et al. .......................... 604/96 |
| 5,156,610 | 10/1992 | Reger . |
| 5,196,024 | 3/1993 | Barath . |

(List continued on next page.)

FOREIGN PATENT DOCUMENTS

| | | |
|---|---|---|
| 3519626A1 | 4/1986 | (DE) . |
| 0 399 712 | 11/1990 | (EP) . |
| 0 567 788 A1 | 3/1993 | (EP) . |
| 1547328 | 6/1979 | (GB) . |
| WO 94/23787 | 10/1994 | (WO) . |

OTHER PUBLICATIONS

Brochure: *Localmed Infusasleeve*, Localmed, 1820 Embarcadero Road, Palo Alto, California 94303, 4 pages.

Primary Examiner—Sharon Kennedy
Assistant Examiner—Jennifer Maynard
(74) Attorney, Agent, or Firm—Nydegger & Associates

(57) ABSTRACT

A method and device for injecting fluid into a treatment area of a vessel wall is provided herein. A first version of the device includes an inflatable balloon mounted on a catheter and a plurality of dispensers extending outwardly and moving with the balloon. At least one fluid passageway connects each injector in fluid communication with a fluid source. During use of the device, the balloon is first positioned in a vessel proximate the treatment area. Next, the balloon is inflated to embed the dispensers into the vessel wall. Subsequently, the fluid from the fluid source is introduced into the fluid passageway and through the dispensers into the treatment area. A second version of the device includes a plurality of flexible tubes mounted between a multi-lumen catheter and a grommet. A push-pull wire is connected to the grommet and passed through a lumen of the multi-lumen catheter. The dispensers are mounted on each of the flexible tubes. During use, the device is first positioned in a vessel. The push-pull wire is then partially withdrawn forcing the grommet to advance towards the multi-lumen catheter. The advancing grommet forces the flexible tubes to bow outwardly, embedding the dispensers into the vessel wall.

9 Claims, 11 Drawing Sheets

U.S. PATENT DOCUMENTS

| | | |
|---|---|---|
| 5,242,397 | 9/1993 | Barath et al. . |
| 5,279,565 * | 1/1994 | Klein et al. ............................ 604/105 |
| 5,282,785 | 2/1994 | Shapland et al. . |
| 5,286,254 | 2/1994 | Shapland et al. . |
| 5,295,962 | 3/1994 | Crocker et al. . |
| 5,306,250 | 4/1994 | March et al. . |
| 5,320,634 | 6/1994 | Vigil et al. . |
| 5,322,508 | 6/1994 | Viera . |
| 5,336,178 * | 8/1994 | Kaplan et al. ........................... 604/53 |
| 5,354,279 | 10/1994 | Hofling . |
| 5,364,356 | 11/1994 | Hofling . |
| 5,370,614 | 12/1994 | Amundson et al. . |
| 5,415,637 | 5/1995 | Khosravi . |
| 5,423,851 | 6/1995 | Samuels . |
| 5,477,857 | 12/1995 | McAfee et al. . |
| 5,571,086 | 11/1996 | Kaplan et al. . |
| 5,599,306 | 2/1997 | Klein et al. . |
| 5,609,574 | 3/1997 | Kaplan et al. . |
| 5,611,767 | 3/1997 | Williams . |
| 5,626,830 | 5/1997 | Sikorska et al. . |
| 5,681,281 | 10/1997 | Vigil et al. . |
| 5,693,029 | 12/1997 | Leonhardt . |
| 5,733,925 * | 3/1998 | Kunz et al. ........................... 514/449 |
| 5,746,716 | 5/1998 | Vigil et al. . |
| 5,747,026 * | 5/1998 | Crapo et al. ........................ 424/94.3 |
| 5,820,583 * | 10/1998 | Demopulos et al. .................. 604/49 |
| 5,861,372 * | 1/1999 | Folkman et al. ......................... 514/2 |
| 5,873,852 * | 2/1999 | Vigil et al. ............................. 604/52 |
| 5,877,289 * | 3/1999 | Thorpe et al. .................... 530/387.1 |
| 5,882,291 * | 3/1999 | Bradshaw et al. ....................... 600/3 |
| 5,900,433 * | 5/1999 | Igo et al. ............................ 514/530 |
| 6,102,904 * | 8/2000 | Vigil et al. ........................... 604/500 |

* cited by examiner

FIG. 3A
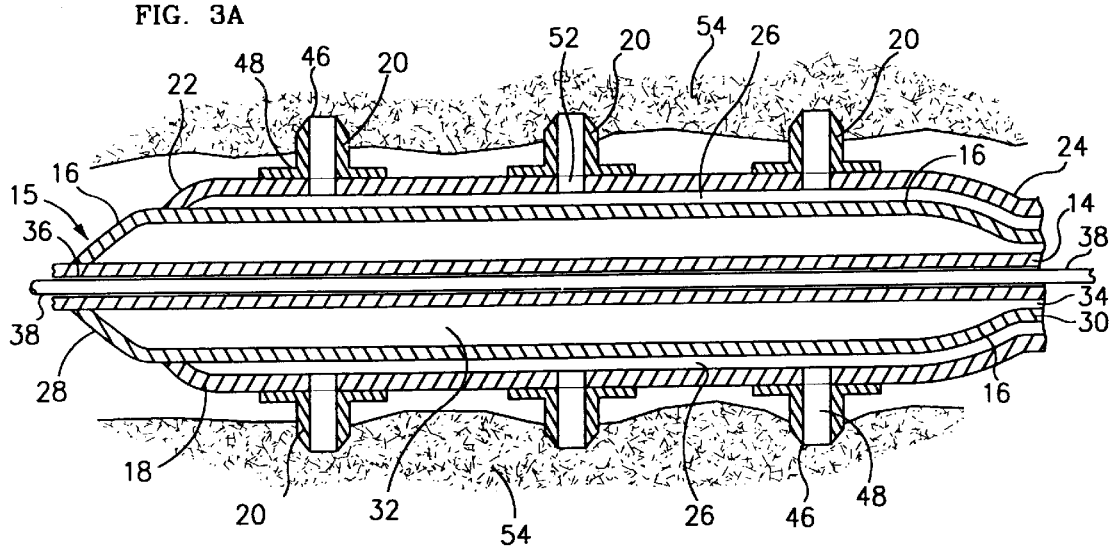
FIG. 3B
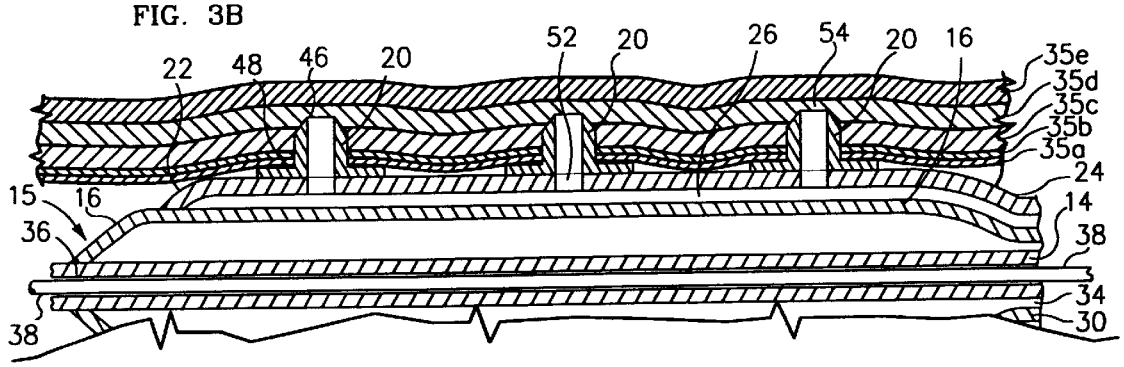
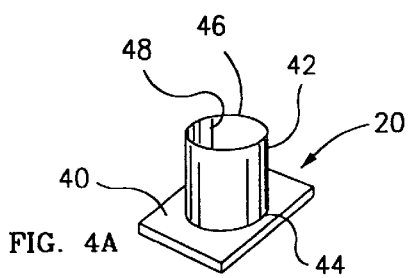
FIG. 4A
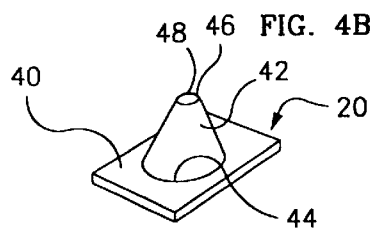
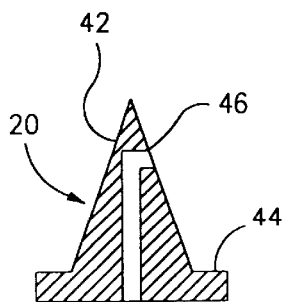
FIG. 4C
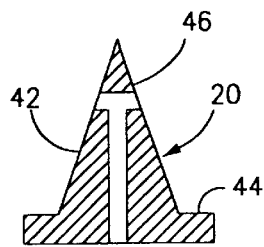
FIG. 4D
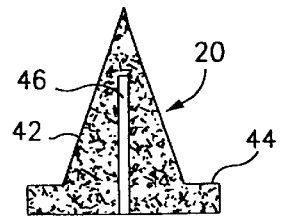
FIG. 4E

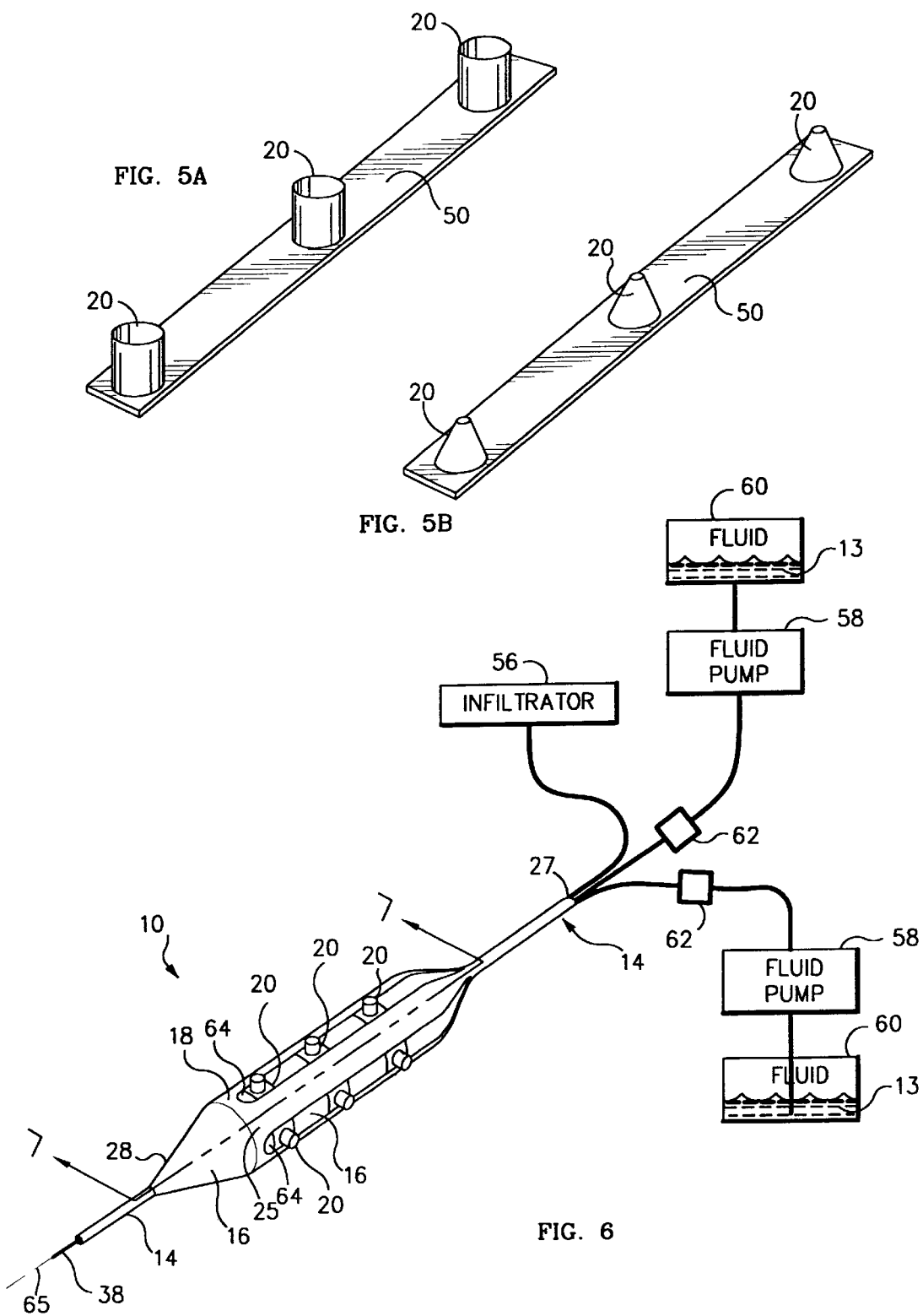

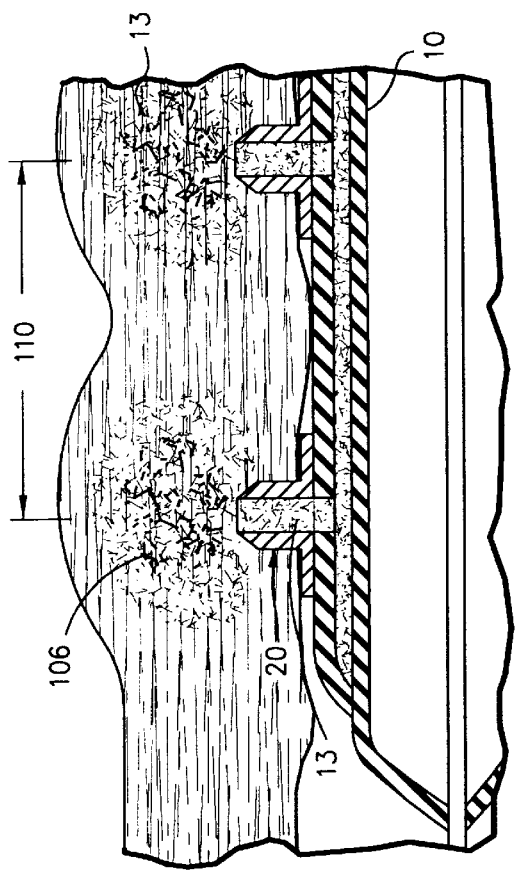
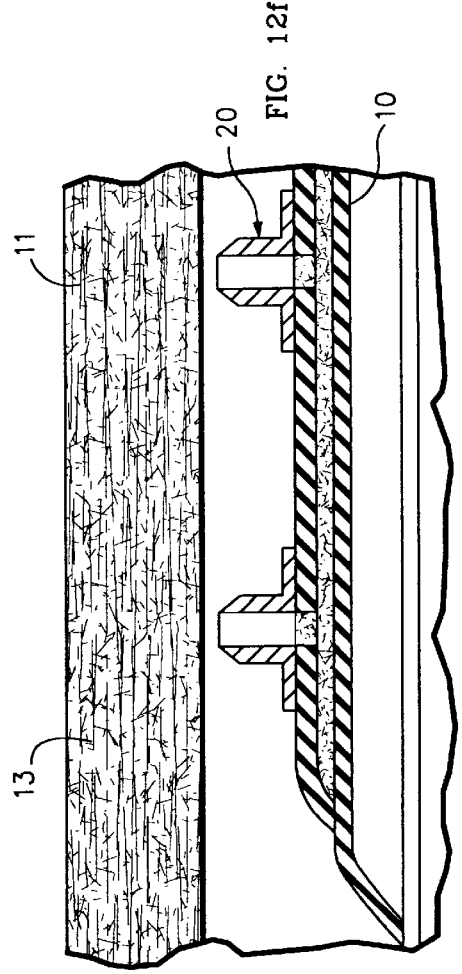
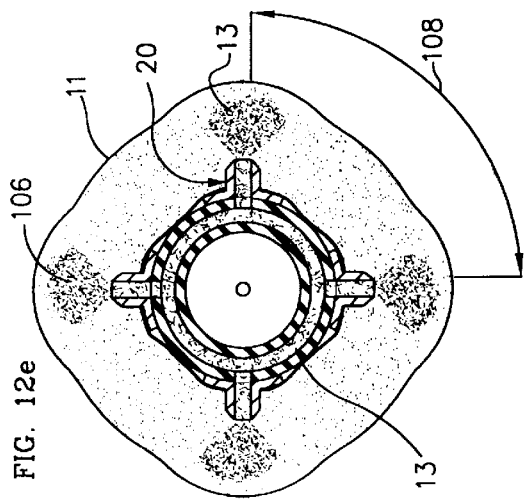
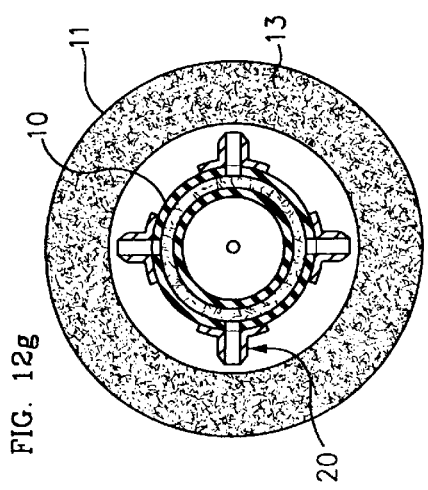
FIG. 12d
FIG. 12e
FIG. 12f
FIG. 12g

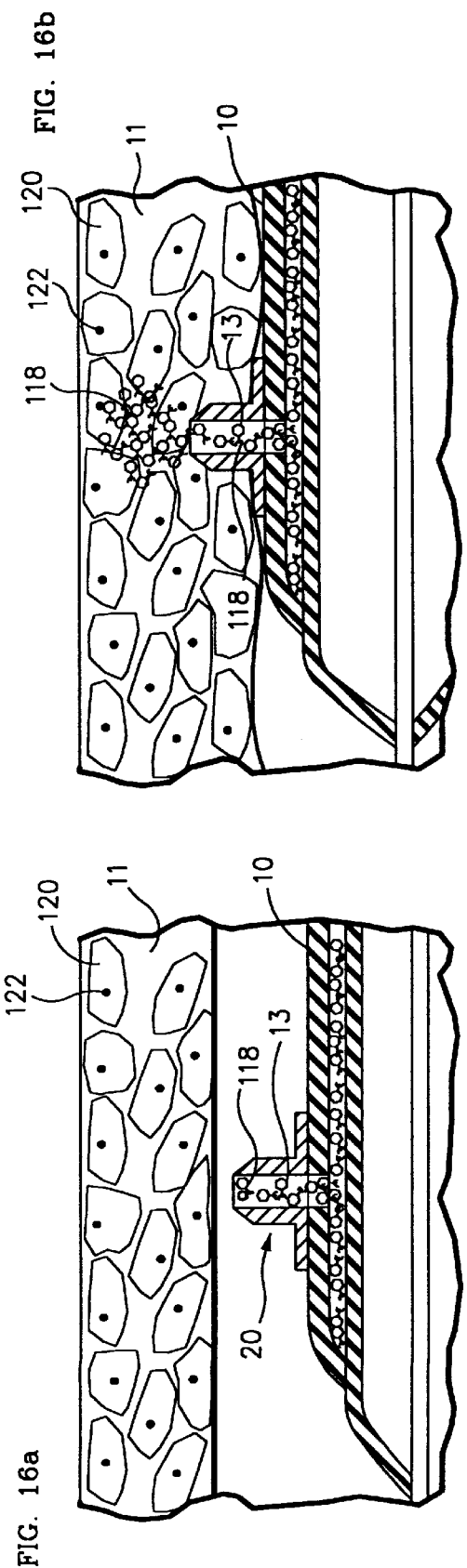
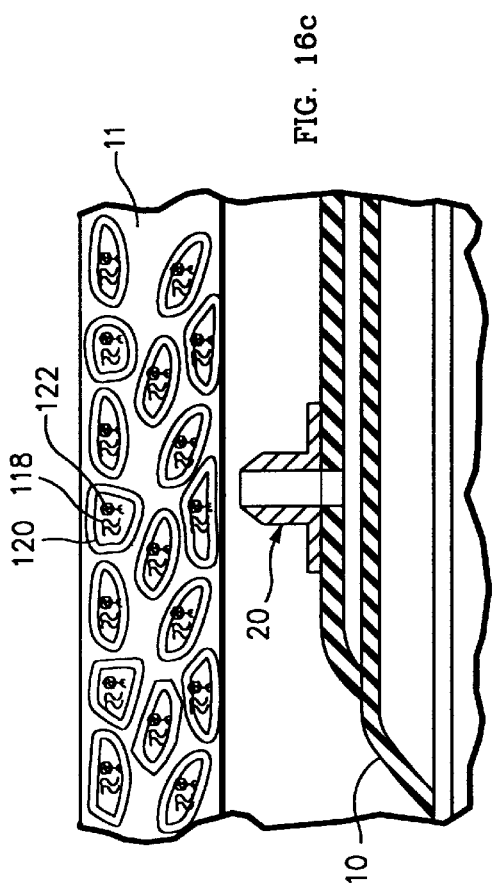

METHOD FOR TREATING A WALL OF A BLOOD VESSEL

FIELD OF THE INVENTION

The present invention pertains generally to medical devices useful for treating a vessel of a patient. More specifically, the present invention pertains to a medical device inserted into a vessel of a patient's cardiovascular system which is useful for injecting a fluid directly into a vessel wall. Additionally, the present invention relates to a number of alternate methods for treating a vessel.

BACKGROUND

Stenosis and/or diseases are a common problem in vessels of a patient. Angioplasty is one procedure used to treat a stenosis within a body vessel of a human being. During an angioplasty procedure, a medical catheter having an inflatable balloon attached to a catheter shaft is advance in the vessel until the balloon is adjacent to the stenosis. Subsequently, the balloon is inflated. This causes the site of the stenosis to compress into the arterial wall and the body vessel to dilate.

However, the angioplasty procedure is not always successful in treating the stenosis in the vessel. Further, the angioplasty procedure can simulate the vessel thereby causing a subsequent restenosis of the vessel. As a result thereof, a number of other devices have been suggested for use in conjunction with an angioplasty procedure. For example, one such device utilizes a balloon to position a plurality of apertures against the vessel wall. Subsequently, the medication is released from the apertures against the endothelium.

Unfortunately, this device has also proved not to be entirely satisfactory. Specifically, with this device, a majority, if not all of the fluid does not penetrate the vessel wall and is washed away into the blood stream. Due to the toxic nature of some fluids, this procedure jeopardizes the health of the patient. Further, because the fluid is washed away, the treatment on the vessel is relatively ineffective.

In light of the above, it is an object of the present invention to provide a device and method useful for treating a stenosis de novo, inhibiting a stenosis from occurring and/or inhibiting a restenosis caused by trauma from an intravascular procedure. It is another object of the present invention to provide a device for treating a vessel having a mechanism for penetrating the vessel wall that is separate from a mechanism which injects a fluid into the vessel wall. Another object of the present invention is to provide a device which can selectively vary the force and depth that is used to penetrate the vessel wall. Still another object of the present invention is to provide a device for treating a vessel which is easy to use, and relatively simple and inexpensive to manufacture. Still another object of the present invention is to provide a device and method for treating a vessel which minimizes the risk to the patient.

SUMMARY

The present invention is directed to a device and method, which satisfies these needs. The device is designed for injecting a fluid from a fluid source into a treatment area of a wall of a vessel. The device includes an expanding member and one or more dispensers. As provided below, the expanding member selectively and accurately controls the movement of the dispensers and the fluid source selectively provides a pressurized supply of fluid to the dispensers. Thus, the mechanism which causes the dispensers to penetrate the vessel wall is separate from the mechanism which releases the fluid into the vessel wall.

Importantly, the present invention can be used to safely treat a stenosis de novo, inhibit a restenosis and/or inhibit a stenosis in a vessel, while minimizing the risk to the patient. Additionally, the present invention is site specific and allows the physician to precisely deliver the fluid only to a precise area of the vessel. This is important because many fluids may have harmful effects on other areas of the body. For example, some fluids may cause blindness.

In a first version of the present invention, the expanding member includes a balloon which is expandable from a contracted, first configuration to an expanded second configuration. The dispensers extend radially from the balloon and move with the balloon between the first configuration and the second configuration. The dispensers preferably penetrate an endothelium layer of the vessel at the treatment area and selectively release the fluid when the balloon is at the second configuration. With this configuration, the depth of penetration of the dispensers into the vessel wall and force used to penetrate the vessel wall is precisely controlled. This allows the present invention to deliver the fluid to the appropriate area of the vessel wall while minimizing trauma to the vessel wall. Further, the balloon can be used to simultaneously dilate the vessel.

At least one fluid passageway connects the fluid source in fluid communication with the dispensers. For example, the fluid passageway can include a flexible tubular sleeve which substantially encompasses and encloses at least a portion of an outer surface of the balloon. The fluid source includes a fluid pump which is in fluid communication with the fluid passageway for selectively providing a pressurized supply of fluid from the fluid source to the dispensers.

Each dispenser can be a substantially tubular protrusion having an attachment end and an invaginating section for invaginating the wall of the vessel. The attachment end includes a base plate which mounts directly onto the tubular sleeve. In some of the embodiments provided herein, the invaginating section is defined by an open edge of the dispenser. In other embodiments, each dispenser can include a porous section or an opening through the dispenser wall which defines the invaginating section.

Depending upon the fluid and the desired treatment, the fluid can be released substantially simultaneously with the dispenser penetrating the treatment area or there can be a time delay between the dispenser penetrating the treatment area and the release of the fluid from the dispensers.

A second version of the expanding member includes a multi-lumen catheter, a grommet, a plurality of flexible tubes which connect the grommet to the catheter and one or more dispensers secured to the flexible tubes. The grommet is movable relative to the catheter to reposition the flexible tubes near the vessel wall.

The invention is also a method for expanding the treatment area and delivering fluid from the fluid source to the treatment area. The method includes advancing the expanding member in the vessel, expanding the expanding member in the vessel and selectively releasing the fluid from the dispenser into the treatment area. The expansion of the expanding member causes the open end of each dispenser to penetrate the treatment area. Additionally, the expansion of the expanding member can also cause simultaneous dilation of the vessel.

The present invention is also a method for treating a wall of a living vessel. The method includes the steps of providing a fluid, advancing an expanding member in the vessel, moving the expanding member to a second configuration so that an invaginating section of a dispenser contacts at least a portion of the wall of the vessel and invaginating at least a portion of the wall of the vessel by selectively releasing the fluid from the invaginating section into the wall of the vessel.

The fluid can be forced from each dispenser into the wall of the vessel at a rate sufficient to create a localized swelling in the wall of the vessel. This allows the fluid to disperse in the wall of the vessel to distribute the fluid in the vessel wall. Preferably, in this embodiment, the dispensers are properly spaced apart to create a plurality of spaced apart localized swellings which subsequently disperse the fluid substantially around a circumference of the wall of the vessel.

The type of fluid can be varied to suit the specific needs of the patient. More specifically, the fluid can be designed to treat a stenosis or disease de novo, inhibit a restenosis by minimizing the effects of a previous intravascular procedure and/or inhibit a stenosis in a vessel. For example, to inhibit a restenosis, the fluid can contain anti-proliferative agents which inhibit the proliferation of smooth muscle cells growth in the vessel in certain pathological conditions. Fluids which selectively kill rapidly dividing cells can be utilized to inhibit the proliferation of smooth tissue growth. Suitable fluids can include anti-proliferative agents such as methotrexate, prednisone, adriamycin, mitomycinc, protein synthesis inhibitors, toxin fragments such as pseudomonas, exotoxin (PE) or Ricin A (RA) Toxin, and radioactive isotopes such as $^{111}$Indium, $^{90}$Yttrium, $^{67}$Gallium, $^{99m}$Tc (Technetium 99), $^{205}$Thallium, and $^{32}$P(Phosphorous 32) radiopharmaceutical. The present device provided is uniquely suited to safely deliver dangerous fluids into the vessel wall while minimizing the amount of fluid which is washed away into the blood stream.

Alternately, for example, a fluid which stimulates the production of collateral vessels can be delivered by the present device. This provides preventative treatment of the patient by creating new collateral vessels in the event the original vessel develops a stenosis. A fluid which includes an angiogenis factor can be utilized for this purpose.

In order to decrease the amount of fluid washed away into the blood stream, a portion of the fluid could precipitate at approximately the vessel pH level of the vessel. Typically, the vessel pH is approximately 7. Thus, a fluid having a fluid pH level of less than approximately 6 or greater than approximately 8 can be utilized. After the fluid is dispensed into the wall of the vessel, the fluid pH level approaches 7 and a portion of the fluid precipitates. In this embodiment, the fluid can include a precipitator, an active component attached to or included within the precipitator and a carrier component which carries the precipitator and the active component. The precipitator precipitates in the wall of the vessel while the carrier component gets washed away into the blood stream. Because the active component is attached to or included within the precipitator, the active component of the fluid remains in the vessel wall. This minimizes the amount of the active component of the fluid which is washed away into the blood stream. For this embodiment, the active component of the fluid, for example, can include an anti-proliferative agent as outlined above. Alternately, the precipitator and active component, for example, can include a radionuclide or radiopharmaceutial precipitate, such as gold colloidal, i.e. $^{198}$Au and $^{199}$Au, and/or an inorganic precipitate.

Additionally, the active component of the fluid can be designed to have a slow, time-release formulation so that active component is released to the vessel wall over an extended period of time. Stated another way, the active component can biodegrade slowly over a period of time to gradually release the active component of the fluid into the vessel wall. A biodegradable polymer could be used to provide a control release formulation to the active component.

Alternately, the fluid could include a binder secured to the active component of the fluid. The binder binds, attaches or crosslinks to at least a portion of the wall of the vessel. The binder can include a ligand which binds to a portion of the vessel wall such as collagen or the smooth muscle cell component of the vessel wall. This ensures that the bulk of the active component of the fluid remains in the vessel wall and minimizes the amount of the active component of the fluid which is washed away into the blood stream. Examples of ligands binding to the vessel wall components include PDGF receptors, adhesive molecules including, but not limited to certain molecules of the integrin family and receptors on activated platelets such thrombin receptors. Alternately, for example, phosphors tridentite which binds to collagen can be utilized. In yet alternate embodiments, the binder can have a direct affinity to form ionic, covalent bonds or Van der Waal attractions to the wall of the vessel or some component thereof.

In still another embodiment, the fluid could be used for gene therapy on the vessel wall. For example, the fluid could include a retroviral, adenoviral vectors or Adenovirus Associated Vectors (AAV) carrying the appropriate DNA payload for appropriate gene switching. The present invention allows for the use of fluids which genetically alter the specific treatment site of the vessel without effecting the rest of the body.

Furthermore, with the present device, the dispensers could be lengthened. This feature allows the present device to deliver a fluid from a vessel, through the vessel wall and into an organ or specific tissue area.

It is important to recognize that a device in accordance with the present invention utilizes a mechanism which causes the dispensers to penetrate the vessel wall that is separate from the mechanism which releases the fluid into the vessel wall. Further, the device can vary the force that is used to penetrate the vessel wall and can simultaneously dilate the vessel wall. Moreover, the unique fluids provided herein minimize the amount of the fluid which is washed away in the blood stream while maximizing the amount of fluid retained in the vessel wall. Additionally, the present invention is particularly useful for injecting radioactive isotopes directly into the vessel wall.

BRIEF DESCRIPTION OF THE DRAWINGS

The novel features of this invention, as well as the invention itself, both as to its structure and its operation will be best understood from the accompanying drawings, taken in conjunction with the accompanying description, in which:

FIG. 3A is a cross-sectional view of the device of FIG. 2 taken on line 3—3 in FIG. 2 positioned in an artery of a patient;

FIG. 3B is an enlarged cross-sectional view of an artery and a plurality of dispensers positioned in the artery of a patient;

FIG. 4A is a perspective view of a first embodiment for a dispenser having features of the present invention;

FIG. 4B is a perspective view of a second embodiment for a dispenser having features of the present invention;

FIG. 4C is a side plan view of a third embodiment of a dispenser having features of the present invention;

FIG. 4D is a side plan view of a fourth embodiment of a dispenser having features of the present invention;

FIG. 4E is a side plan view of a fifth embodiment of a dispenser having features of the present invention;

FIG. 5A is a perspective view of an embodiment of a plurality of dispensers having features of the present invention;

FIG. 5B is a perspective view of another embodiment of a plurality dispensers having features of the present invention;

FIG. 6 is a perspective view of another embodiment of a device having features of the present invention;

FIG. 12D illustrates a longitudinal cross-sectional view of the vessel wall after the fluid has been injected into the vessel wall;

FIG. 12E is an axial cross-sectional view illustrating the fluid dispensers injected into the vessel wall;

FIG. 12F is a longitudinal cross-sectional view of a portion of the vessel and the device illustrating the fluid dispersed in the vessel wall;

FIG. 12G is an axial cross-sectional view of the vessel and the device illustrating the fluid dispersed in the vessel wall;

FIG. 16A is a longitudinal cross-sectional view of a vessel illustrating the cell genes of the vessel and a portion of the device having features of the present invention;

FIG. 16B is a longitudinal cross-sectional view of a vessel illustrating a fluid including a virus gene being injected into the wall of the vessel by the device; and FIG. 16C is a longitudinal cross-sectional view of a portion of the vessel which illustrates that the virus gene has attacked the cell genes and replaced the cell genes within the cell.

DESCRIPTION

Figure 1:
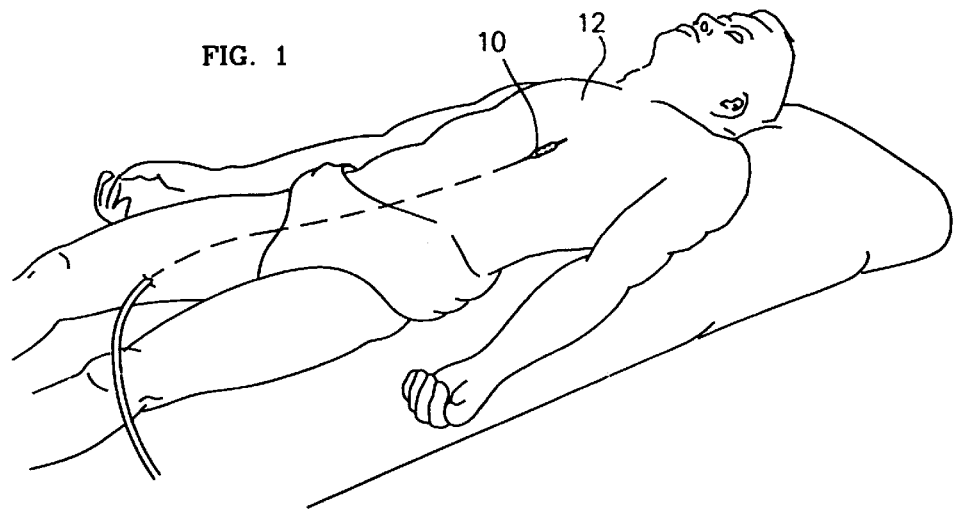
FIG. 1 is a perspective view of a patient with a device having features of the present invention positioned in an artery of the patient.

Referring initially to FIG. 1, a device 10 for injecting a fluid 13 into a wall of a living blood vessel 11 in accordance with the present invention is shown positioned in an upper body, blood vessel 11 of a patient 12. However, the device 10 can be used in arteries and vessels throughout the patient 12. Importantly, as provided in detail below, the device 10 provided herein, allows for substantially symmetrical injection of the fluid 13 directly in the vessel 11 around the circumference of the vessel 11.

Figure 2:
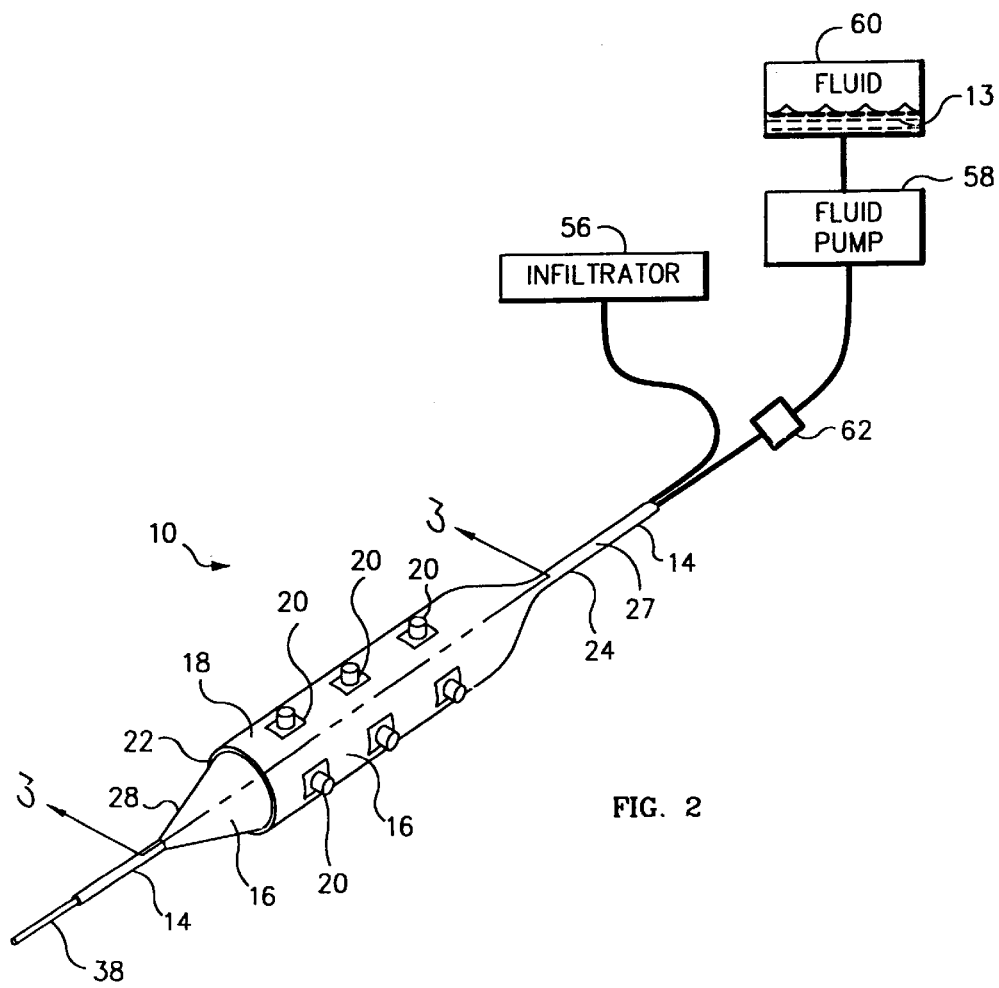
FIG. 2 is a perspective view of a device having features of the present invention.

Referring to FIG. 2, a first version of a device 10 having features of the present invention includes a multi-lumen catheter 14, an expanding member 15 mounted thereon, a tubular sleeve 18 and a plurality of dispensers 20.

As illustrated in FIGS. 2 and 3A, the expanding member 15 can be an inflatable balloon 16. The balloon 16 is at least inflated and deflated between a first, substantially retracted configuration and a second, substantially expanded configuration. The balloon 16 when at the first configuration is substantially deflated. The balloon 16 when at the second configuration can be anywhere from the partially inflated to fully inflated depending upon the size of the vessel 11. The balloon 16 and tubular sleeve 18 can be made of a number of materials including polyethylene terephthalate (PET).

Further, FIG. 2 indicates that the tubular sleeve 18 surrounds a substantial portion of the balloon 16, and that a plurality of dispensers 20 are mounted onto the tubular sleeve 18. Of these, the dispensers 20 illustrated are only exemplary.

A more complete appreciation of the structural cooperation between balloon 16, tubular sleeve 18 and the dispensers 20 is provided by FIG. 3A wherein, it will be seen that a distal end 22 of tubular sleeve 18 is attached directly to an outer surface 25 of balloon 16. FIG. 3A also shows that the tubular sleeve 18 substantially surrounds and encloses the balloon 16 and that a proximal end 24 of tubular sleeve 18 extends proximally from and beyond the balloon 16 over catheter 14. The tubular sleeve 18 cooperates with the outer surface 25 of the balloon 16 to define a portion of a fluid passageway 26. The proximal end 24 can be connected to an outer lumen 27 (not shown in FIG. 3A) of the catheter 14 to complete the fluid passageway 26.

FIG. 3A further shows that the distal end 28 of balloon 16 is affixed to the catheter 14, and that the proximal end 30 of the balloon 16 attaches onto the catheter 14 to create an inflation chamber 32 in the interior of the balloon 16. A balloon port 34 provides fluid access into the inflation chamber 32. For purposes of the present invention, the balloon port 34 can be connected in fluid communication with a balloon lumen (not shown) of the catheter 14. FIG. 3A also shows that catheter 14 is formed with an inner lumen 36 which is dimensioned to receive a guidewire 38 therethrough.

The blood vessel 11 includes multiple layers. To facilitate the present discussion, some of the layers, namely, an endothelium layer 35a, a basement membrane layer 35b, a lamina layer 35c, a media layer 35d, and an adventitia layer 35e are illustrated in FIG. 3B. The basement membrane layer 35b, the lamina layer 35c, the media layer 35d shall be considered internal layers. Importantly, with the present device 10, the depth of penetration of dispenser 20 can be precisely controlled by controlling the length of each dispenser 20. Thus, the device 10 is able to deliver the fluid 13 to a desired, target layer of the blood vessel 11. For example, as illustrated in FIG. 3B, the dispenser 20 penetrates the endothelium layer 35a, the basement membrane layer 35b, and the lamina layer 35c and precisely delivers the fluid 13 to the media layer 35d, i.e. the target layer in this example. Alternately, for example, a shorter dispenser 20 could be utilized to deliver the fluid 13 to the lamina layer 35c. Additionally, with the present invention, the device 10 can be used to simultaneously dilate the vessel 11.

Referring now to FIG. 4A, each dispenser 20 includes a base plate 40 and a tubular protrusion 42 having an attachment end 44 and an invaginating section 46. Further, it is seen that the attachment end 44 of the tubular protrusion 42 affixes to and is an integral part of the base plate 40. Preferably, the dispenser 20 is made of nickel and the tubular protrusion 42 is formed by punching out the base plate 40. In the embodiment illustrated in FIG. 4A, the invaginating section 46 is defined by an opening which is opposite the base plate 40. The tubular protrusion 42 defines a fluid channel 48 which extends through the dispenser 20. Each dispenser 20 shown in FIG. 4A is substantially annular shaped.

FIG. 4B shows another embodiment of the dispenser 20. Each tubular protrusion 42 shown in FIG. 4B is substantially conical shaped. Similarly, the dispenser 20 in FIG. 4B is preferably made of nickel and is formed to have a fluid channel 48 which extends through the injector 20.

FIGS. 4C and 4E illustrate additional, alternate embodiments of the dispenser 20. In the embodiment illustrated in FIGS. 4C through 4E, the tubular protrusion 42 is substantially conical shaped. However, in FIG. 4C, the invaginating section 46 is defined by an opening which extends through the side of the tubular protrusion 42. Somewhat similarly, in FIG. 4D, the invaginating section 46 is defined by a pair of openings which extend through a side of each tubular protrusion 42. This feature inhibits plugging of the invaginating section 46 during insertion into the vessel 11. In FIG. 4E, the tubular protrusion 42 is made of a porous material. Thus, the porous material defines the invaginating section 46 of each dispenser 20. Basically, in this embodiment, the fluid 13 is forced through the porous tubular protrusion 42.

FIG. 5A shows a plurality of dispensers 20 formed upon the same base plate 50. Specifically, FIG. 5A shows an elongated base plate 50 from which the dispenser 20 have been formed. In all important respects, the dispenser 20 shown in FIG. 5A are structurally the same as the dispensers 20 discussed above with reference to FIG. 4A. The only difference being that they are collectively mounted on the same base plate 50.

Similarly, FIG. 5B shows a plurality dispensers 20 formed upon the same base plate 50. In all important respects, the dispensers 20 shown in FIG. 5B are structurally the same as the dispenser 20 discussed above with reference to FIG. 4B. Again, the only difference being that they are collectively mounted on the same base plate 50.

Referring back to FIG. 3A, the dispensers 20 are mounted onto the tubular sleeve 18 so that the fluid channel 48 of each respective dispenser 20 is aligned with a hole 52 in the tubular sleeve 18. This is done to establish fluid communication between the particular dispenser 20 and the infusion chamber 26. As a practical matter, it may be preferable in the construction of the device 10 to first mount the dispenser 20 onto the tubular sleeve 18, which can be done in any manner well known in the pertinent art, such as by bonding, and then pierce the tubular sleeve 18 through the dispenser 20.

The dispensers 20 of the present invention extend between about 0.005 inches and about 0.02 inches away from the tubular sleeve 18 when the balloon 16 is inflated. However, those skilled in the art will recognize that these distances are merely exemplary.

In another embodiment of the present invention shown in FIG. 6, the basic components of the device 10 include the multi-lumen catheter 14 formed to accommodate the guide wire 38, the balloon 16, the plurality of dispensers 20 and a plurality of tubular channels 64 mounted on the outer surface 25 of balloon 16. Each tubular channel 64 has a smaller diameter than the balloon 16 and is positioned to be substantially parallel with a longitudinal axis 65 of the balloon 16.

FIG. 6 further shows that mounted on the surface of each tubular channel 64 is the dispensers 20. The dispensers 20 are positioned on the surface of tubular channel 64 so that when balloon 16 is inflated, the dispensers 20 move outwardly in a radial direction. Note, however, the showing of dispensers 20 is for illustration purposes only and it should be appreciated that any dispenser 20 or combination of dispensers 20 discussed in association with the previous embodiments may be used.

Figure 7:
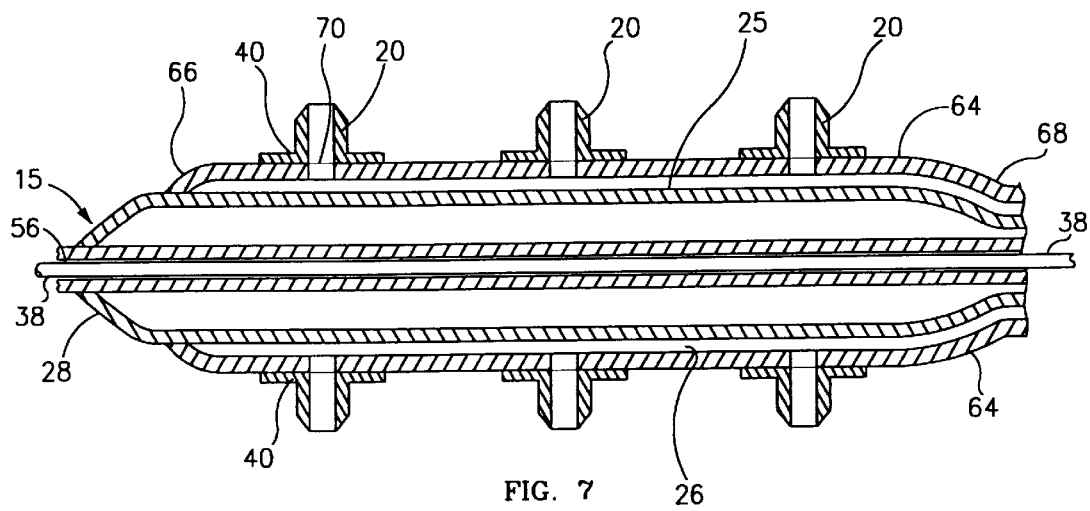
FIG. 7 is a cross-sectional view taken on line 7—7 of FIG. 6.

Referring now to FIG. 7, the cross-sectional view of device 10 shows the tubular channel 64 in more detail. More specifically, a distal end 66 of tubular channel 64 is sealed to create a portion of the fluid passageway 26 which connects the dispensers 20 to the fluid source 60. Referring to FIGS. 6 and 7, it is appreciated that the proximal end 68 of the tubular channel 64 is in fluid communication with the outer lumen 27 of the catheter, which is connected in fluid communication with the fluid pump 58 and the fluid source 60.

Returning to FIG. 7, the dispensers 20 are shown mounted on the surface of tubular channel 64. As FIG. 7 further shows in detail, base 40 of each dispenser 20 is mounted on the tubular channel 64 over a corresponding hole 70. From this view, it can be appreciated that any number of tubular channels 64 could be mounted on the external surface of balloon 16. It is further appreciated that any number of dispensers 20 could be mounted on a single tubular channel 64.

Figure 8:
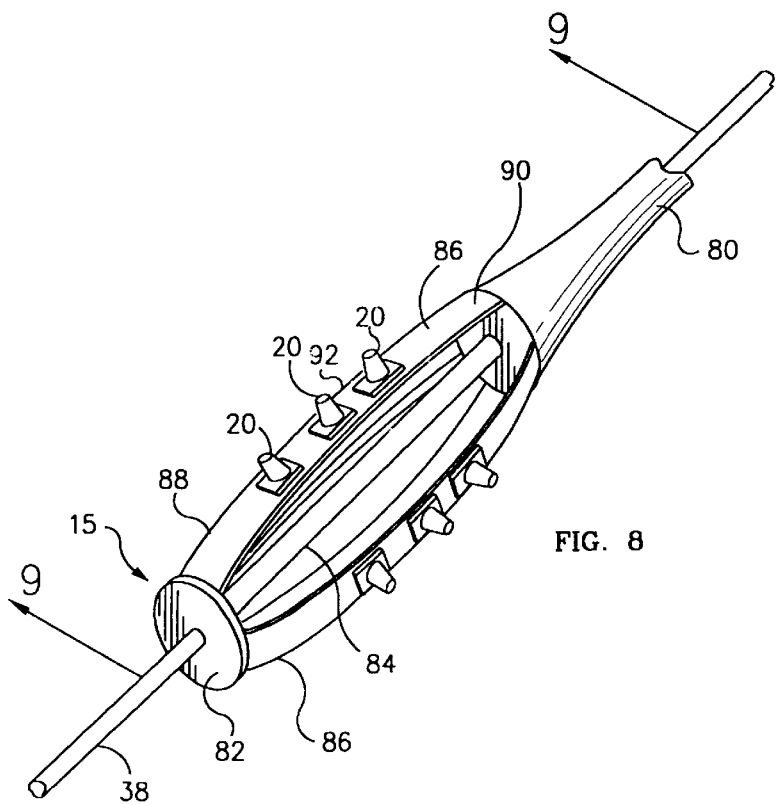
FIG. 8 is a perspective view of yet another embodiment of a device having features of the present invention.

FIG. 8 shows a second version of the expanding member 15 which includes a multi-lumen catheter 80 and a grommet 82. Both the multi-lumen catheter 80 and the grommet 82 are disposed about the same longitudinal axis with the grommet 82 positioned distally, and separated from, the distal end of the multi-lumen catheter 80.

Some type of apparatus is used to move the grommet 82 translationally along the longitudinal axis. For example, referring to FIG. 8, a push-pull wire 84, is shown connected to the grommet 82. The push-pull wire 84 extends through one of the lumens of the multi-lumen catheter 80 allowing the push-pull wire 84 to move translationally in line with the longitudinal axis. The translational movement of the push-pull wire 84 causes the grommet 82 to undergo a similar translational displacement. In many cases, it will be desirable to use the device 10 of the present invention in combination with the guidewire 38. In such cases, the push-pull wire 84 may be formed with an internal lumen through which the guidewire 38 may be passed.

In the second version, a plurality of hollow, flexible tubes 86 are attached between the grommet 82 and the multi-lumen catheter 80. Each of the flexible tubes 86 includes a distal end 88, a proximal end 90 and a central region 92. The proximal end 90 of each tube 86 is joined to the multi-lumen catheter 80. The distal end 88 of each tube 86 is joined to the grommet 82. Preferably, the tubes 86 are distributed radially around the multi-lumen catheter 80 and grommet 82 in a manner substantially as shown in FIG. 8.

Figure 9:
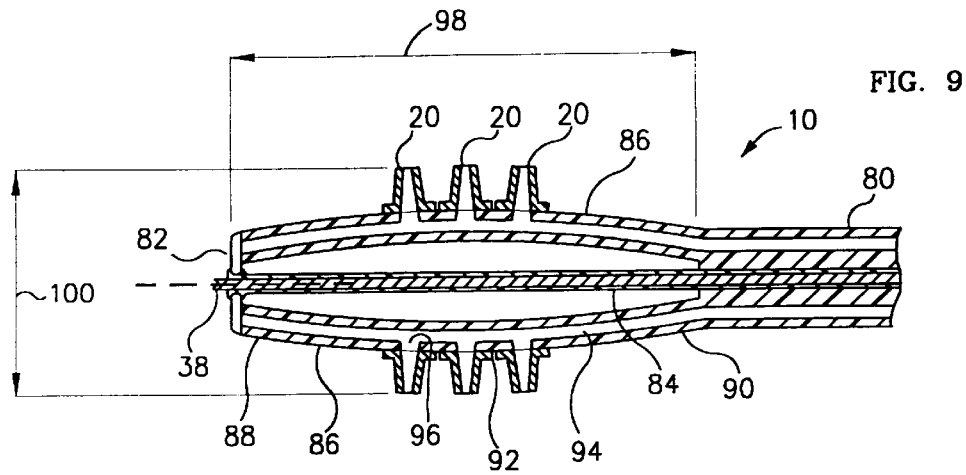
FIG. 9 is a cross-sectional view of the device of FIG. 8 shown in a retracted configuration, as seen along line 9—9 in FIG. 8.
Figure 10:
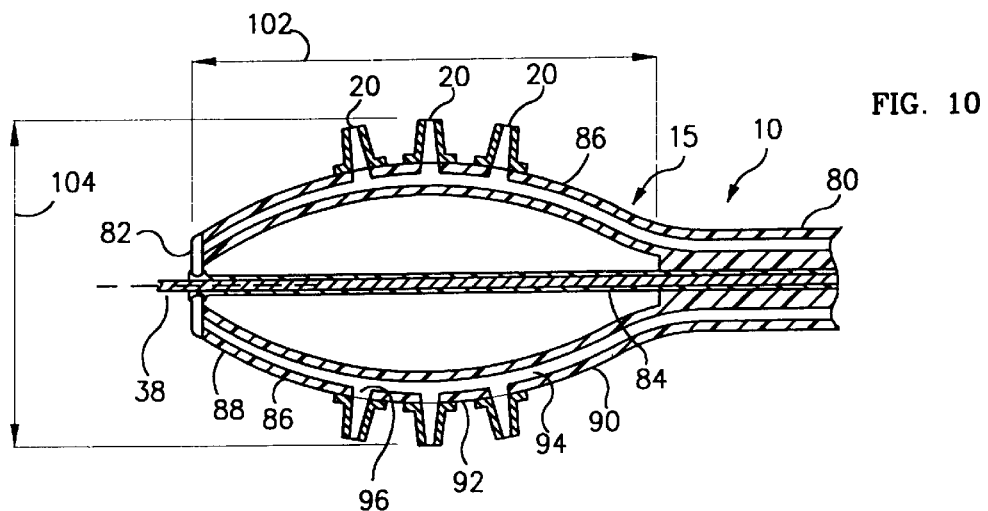
FIG. 10 is a cross-sectional view of the device of FIG. 8 shown in an expanded configuration, as seen along the line 9—9 in FIG. 8.
Figure 11:
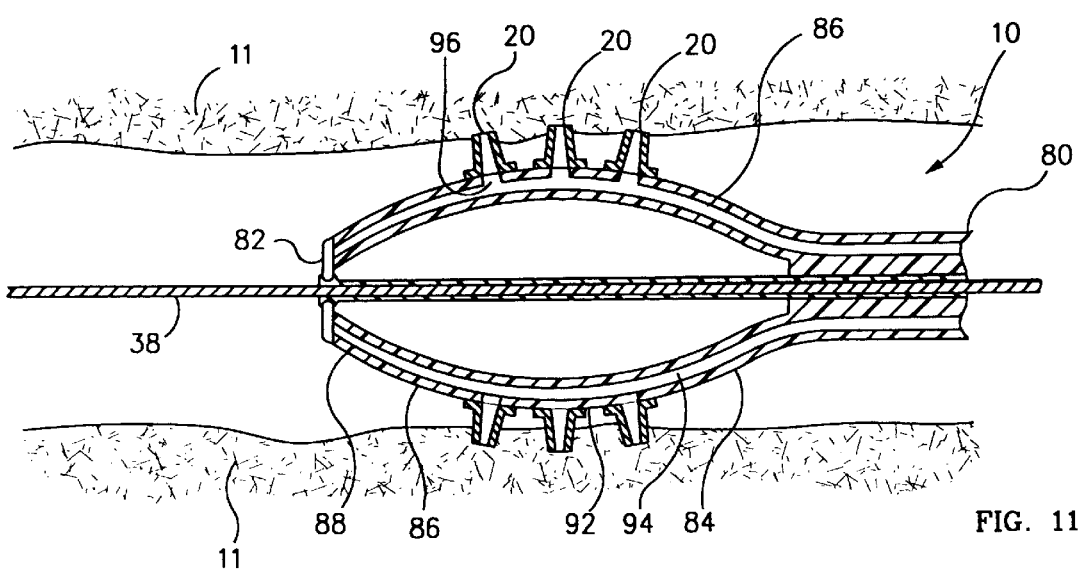
FIG. 11 is a cross-sectional view of the device of FIG. 8 positioned in a blood vessel of the patient.

Referring now to FIGS. 9–11, it may be seen that each flexible tube 86 is formed with a lumen 94. The lumen 94 of flexible tubes 86 passes through flexible catheter 80 allowing fluid 13 to be passed through multi-lumen catheter 80 and into flexible tubes 86. The lumen 94 of each flexible tube 86 passes separately through multi-lumen catheter 80 allowing a different fluid 13 to be passed into each flexible tube 86. Alternatively, the lumen 94 of each flexible tube 86 may be attached to one or more common lumens within multi-lumen catheter 80.

FIGS. 9 and 10 also show that the plurality of dispensers 20 are attached to the central region 90 of each tube 86. Each flexible tube 86 is formed with a plurality of holes 96 which correspond to a respective dispenser 20. Functionally, each hole 96 connects the channel of a respective dispenser 20 to lumen 94 allowing the fluid pump 58 to pump fluid 13 from the fluid source 60 into lumen 94 to be expelled through the dispensers 20.

FIGS. 9, and 10 also show that the present invention is movable between the first, contracted configuration (shown in FIG. 9) and the second, expanded configuration (shown in FIG. 10). In greater detail, it may be seen that the grommet 82 and the multi-lumen catheter 80 are distanced by a first separation distance 98. The device 10 shown in FIG. 9 also has a first overall width designated 100. In comparison, the grommet 82 and the multi-lumen catheter 80, shown in FIG. 10 is distanced by a second separation distance 102 which is smaller than the first separation distance 98 of FIG. 9. The device 10, shown in FIG. 10 also has a second overall width 104 which is greater than the first overall width 100 shown in FIG. 9.

The difference between the first, contracted configuration shown in FIG. 9 and the second, expanded configuration shown in FIG. 10 is accomplished, by translational movement of the grommet 82 along the longitudinal axis. In more detail, as the push-pull wire 84 causes the grommet 82 to move towards the multi-lumen catheter 80, each of the flexible tubes 86 bows outwardly away from the longitudinal axis. In this fashion, the push-pull wire 84 may be used to move the grommet 82 translationally to cause the flexible tubes 86 to alternately bow, as seen in FIG. 10, and straighten, as seen in FIG. 9. In some cases, it will be preferable to fabricate the flexible tubes 86 from resilient material which biases the tubes 86 into either the bowed or straight configuration.

Figure 12C:
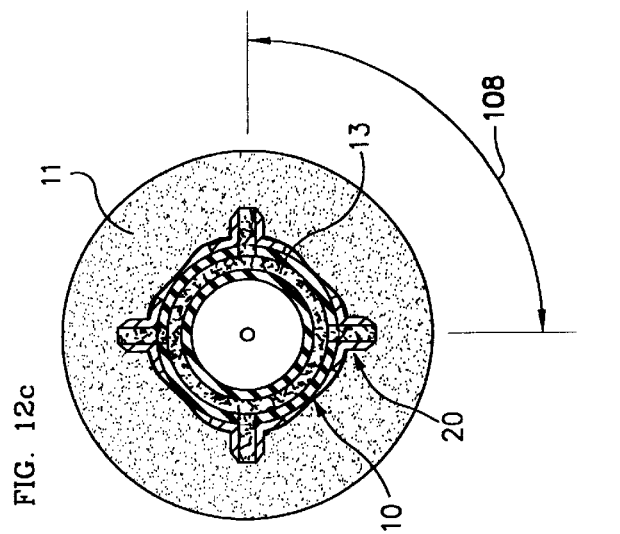
FIG. 12C is an axial cross-sectional view of the vessel and the device illustrating the dispensers penetrating the vessel wall.
Figure 12A:
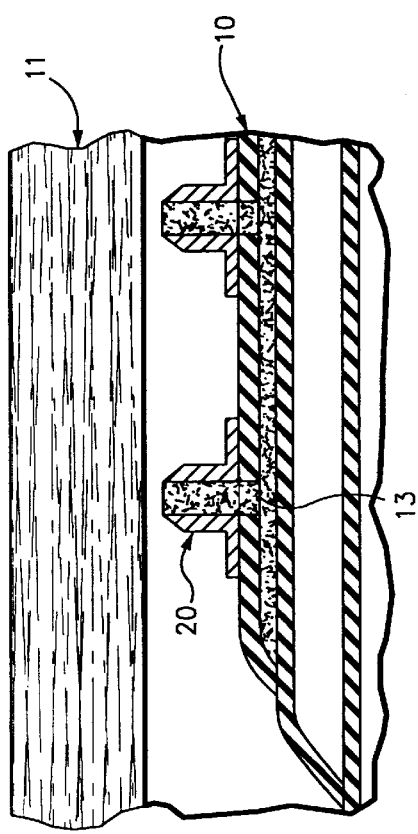
FIG. 12A is a longitudinal cross-sectional view of a portion of the vessel and a device prior to the dispensers penetrating the vessel wall.
Figure 12B:
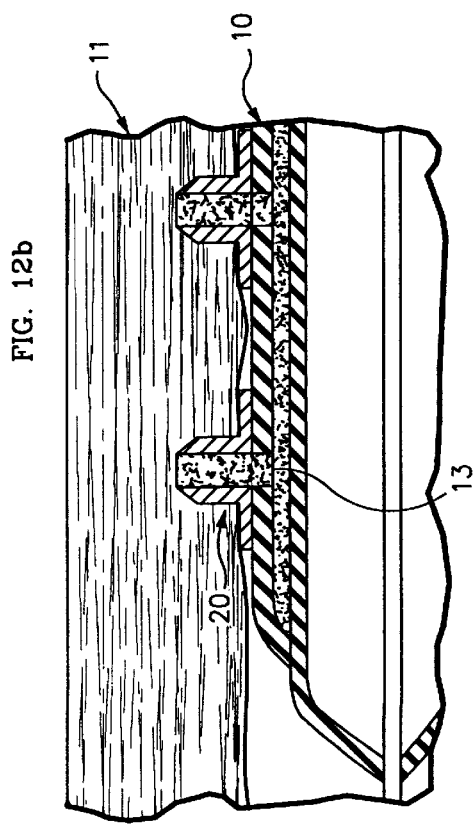
FIG. 12B is a longitudinal cross-sectional view of a portion of the vessel and a portion of the device after the dispensers penetrate the vessel wall.

Referring to FIGS. 12a–12f, the fluid 13 can be forced from each dispenser 20 into the wall of the vessel 11 at a rate sufficient to create a localized swelling 106 in the wall of the vessel 11. This allows the fluid 13 to disperse in the wall of the vessel 11 and distribute around the circumference of the vessel 11. Preferably, as illustrated in FIG. 12a and 12f, the dispensers 20 are spaced apart to create a plurality of spaced apart localized swellings 106 which subsequently disperse the fluid 13 substantially around a circumference of the wall of the vessel 11. The rate required to create a localized swelling 106 depends upon the viscosity fluid 13 utilized. Typically, between approximately 400 microliters and 700 microliters of the fluid 13 is dispensed in between approximately five and forty-five seconds is sufficient to create the desired localized swelling. However, it should be recognized that the amounts and time frames provided herein are merely exemplary. The time frame and amount required to cause the desired localized swelling varies according to a number of factors, such as the viscosity of the fluid 13.

The spacing required to create a plurality of spaced apart localized swellings 106 which subsequently disperse the fluid 13 along the treatment area 54 also vary according to the fluid 13 utilized. It is believed that the dispensers 20 should be spaced a circumferential distance 108 of between approximately 1 millimeter and 6 millimeters, roughly 70 degrees and 140 degrees apart. Further, the dispensers 20 should be spaced apart a longitudinal distance 110 of between approximately 0.5 millimeters and three millimeters.

The composition of the fluid 13 to be injected into the vessel 11 depends upon the treatment being performed and the physical characteristics of the patient 12. More specifically, the fluid 13 can be designed to treat a stenosis or disease de novo, inhibit a restenosis by minimizing the effects of a previous intravascular procedure and/or inhibit a stenosis in a vessel 11. For example, to inhibit a restenosis, the fluid 13 can contain anti-proliferative agents which inhibit the proliferation of smooth muscle cells growth in the vessel in certain pathological conditions. These fluids selectively kill rapidly dividing cells can be utilized to inhibit the proliferation of smooth tissue growth. Suitable fluids can include anti-proliferative agents such as methotrexate, prednisone, adriamycin, mitomycinc, protein synthesis inhibitors, toxin fragments such as pseudomonas, exotoxin (PE) or Ricin A (RA) Toxin, and radioactive isotopes 112 such as $^{111}$Indium, $^{90}$yttrium, $^{67}$Gallium, $^{99m}$Tc (Technetium 99), $^{205}$Thallium, and $^{32}$P (Phosphorous 32) radiopharmaceutical. It is believed that the present device provided is uniquely suited to safely deliver dangerous fluids 13 into the vessel wall 11 while minimizing the amount of fluid 13 which is washed away into the blood stream.

Alternately, for example, a fluid 13 which stimulates the production of collateral vessels can be delivered by the present device. This feature allows for the preventative treatment of the patient by creating new collateral vessels in the event the original vessel develops a stenosis. A fluid which includes an angiogenis factor can be utilized for this purpose.

Figure 13B:
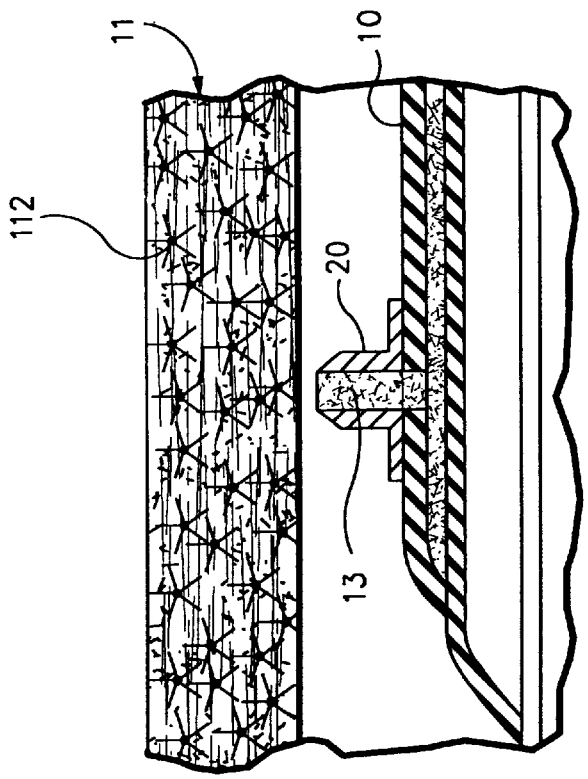
FIG. 13B is a longitudinal cross sectional view of a portion of the vessel and the device after the fluid containing a radioactive isotope is dispersed into the vessel wall.
Figure 13A:
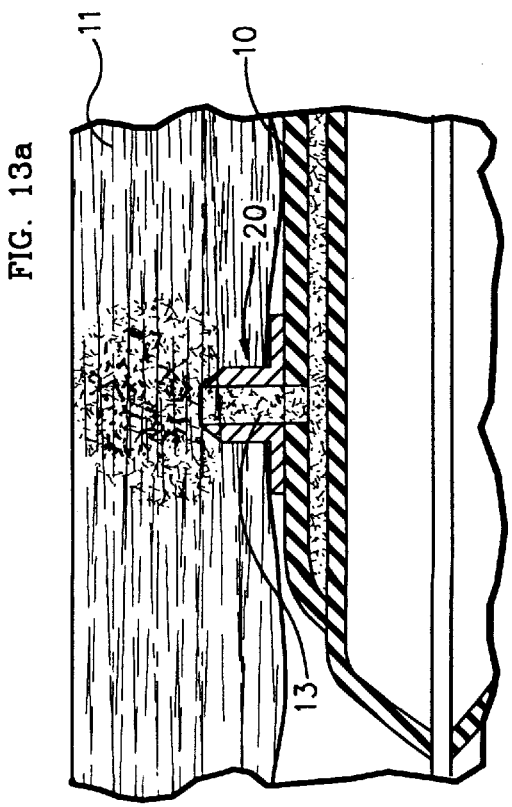
FIG. 13A is a longitudinal cross sectional view of the vessel and a device illustrating a fluid containing a radioactive isotope being dispersed into the vessel wall.

FIGS. 13a and 13b, illustrate the fluid 13 including a radioactive isotope 112 which can reduce and inhibit tissue and/or cell growth of the vessel 11. Because the radioactive isotopes 112 are injected directly in the vessel 11 and are symmetrically injected around the circumference of the vessel 11, relatively low energy radioactive isotopes 112 having a relatively short half life can be utilized. These relatively low energy radioactive isotopes 112 should cause minimal trauma to the patient 12. The device 10 provided herein is uniquely suited to safely deliver a radioactive isotope 112 to only the treatment area 54 of the vessel wall 11, while minimizing the amount of radioactive isotope 112 which is washed away into the blood stream. Additionally, the radioactive isotope 112 can be encapsulated within a suitable carrier such as amino-mannose modified liposome, which is rapidly absorbed into smooth muscle cells of the lamina layer 35c.

The exact dose of radiation to be delivered to the vessel 11 can be varied to suit the needs of the patient. It is presently believed that a tissue absorbed dose of between approximately 8–40 Gray will be utilized to inhibit restonosis. The exact amount of fluid 13 and type of fluid 13 injected into the vessel 13, can be varied to account for fluid 13 washed into the blood stream and/or account for the active life of the fluid 13.

Figure 14B:
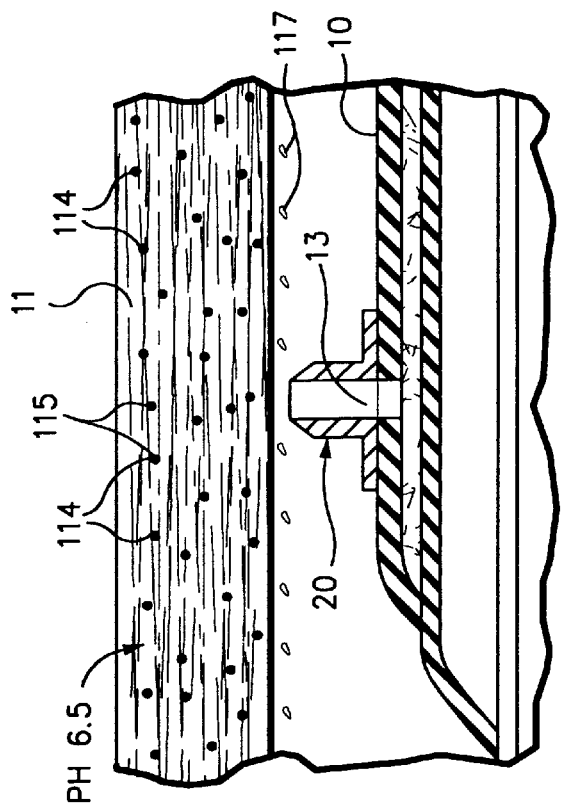
FIG. 14B is a longitudinal cross-sectional view of a portion of the vessel and the device after a portion of the fluid precipitates.
Figure 14A:
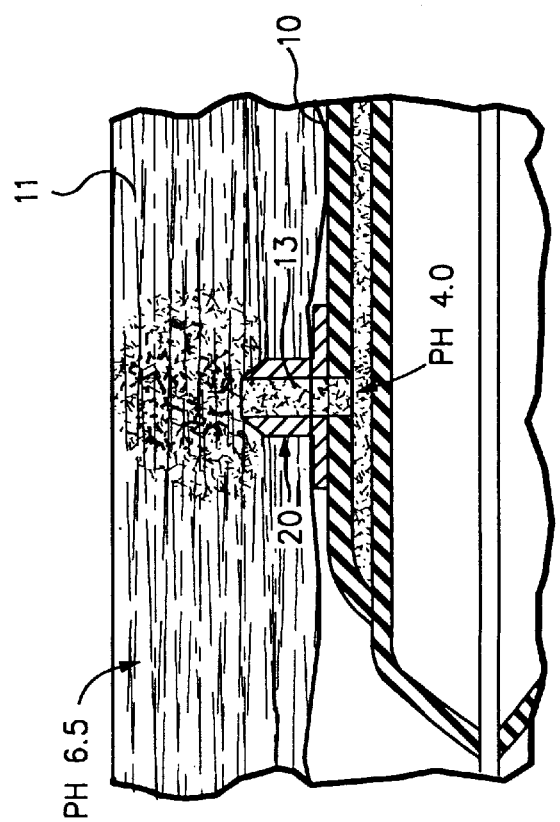
FIG. 14A is a longitudinal cross-sectional view of the vessel and a device illustrating a fluid containing a precipitant being dispersed into the vessel wall.

Referring to FIGS. 14a and 14b, in order to minimize the amount of fluid 13 which is washed away into the blood stream, a portion of the fluid 13 could precipitate at approximately the vessel pH level of the vessel. Typically, the vessel pH is approximately 7. Thus, a fluid 13 having a fluid pH level of less than approximately 6 or greater than approximately 8 can be utilized. After the fluid 13 is dispensed into the wall of the vessel 11, the fluid pH level approaches 7 and a portion of the fluid 13 precipitates. For this embodiment, the fluid 13 could include a precipitator 114, an active component 115 attached to or incorporated within the precipitator 114 and a carrier component 117 which carries the precipitator 114 and the active component 115. The active component 115 is the portion of the fluid 13 which is designed to treat the patient 12. In this example, the precipitator 114 could precipitate in the wall of the vessel 11 while the carrier component 117 gets washed away into the blood stream.

Because the active component 115 is attached to or incorporated within the precipitator 114, this ensures that the bulk of the active component 115 of the fluid 13 remains in the vessel wall 11 and minimizes the amount of the active component 115 of the fluid 13 which is washed away into the blood stream. In this embodiment, the active component 115 of the fluid 13, for example, can include an anti-proliferative agent as outlined above. Alternately, the precipitator 114 and the active component 115 can be a radionuclide or radiopharmaceutial precipitate, such as gold colloidal, i.e. $^{198}$Au and $^{199}$Au, and/or an inorganic precipitate such as organometalic precipitate.

Additionally, the active component 115 of the fluid 13 can be designed to have a slow, time-release formulation so that active component 115 is released to the vessel wall 11 over an extended period of time. Stated another way, the active component 115 can biodegrade slowly over a period of time to release the active component of fluid 13 into the vessel wall 11 over an extended period of time. A biodegradable polymer could be used to provide a control release formulation to the active component 115.

Figure 15B:
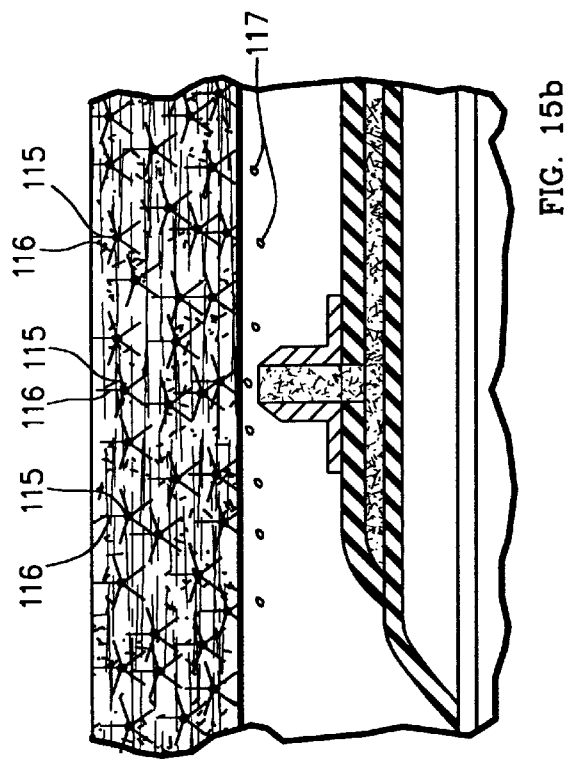
FIG. 15B is a longitudinal cross-sectional view of a portion of the vessel and the device illustrates a binder binding to a portion of the vessel wall.
Figure 15A:
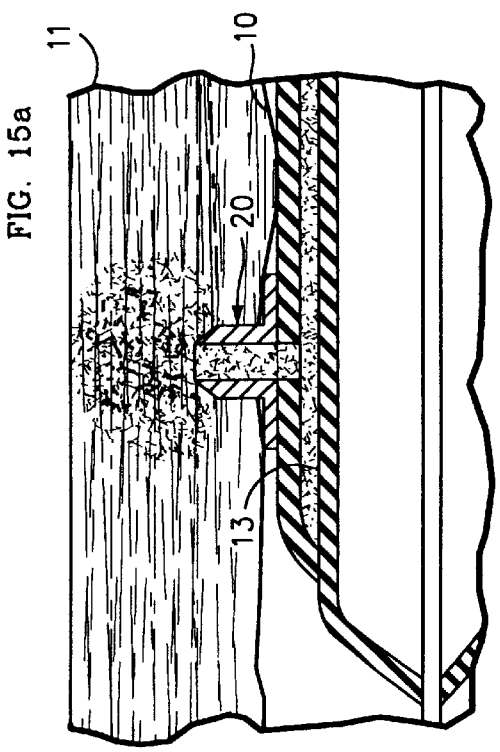
FIG. 15A is a longitudinal cross-sectional view of a portion of the vessel and the device illustrating a fluid with a binder being injected into the vessel wall.

Alternately, referring to FIGS. 15A and 15B, the fluid 13 could include a binder 116, the active component 115 and the carrier component 117. The binder 116 is secured to the active component 115 of the fluid 13. The binder 116 is adapted to bind, attach and/or crosslink to at least a portion of the wall of the vessel 11. For example, the binder 116 could include a ligand which binds to a portion of the vessel wall 11 such as collagen or the smooth muscle cell component of the vessel wall. Because the binder 16 is secured to the active component 115, this ensures that the bulk of the active component 115 of the fluid 13 remains in the vessel wall 11 and minimizes the amount of the active component 115 of the fluid 13 which is washed away into the blood stream. Examples of ligands binding to the arterial wall components include PDGF receptors, adhesive molecules including, but not limited to certain molecules of the integrin family and receptors on activated platelets such thrombin receptors. Another type of ligand is sold under the name Ceretec® by Amersham located in Arlington Heights, Ill. Alternately, for example, phosphors tridentite which binds to collagen can be utilized. In yet an alternate embodiment, the binder 116 can have a direct affinity to form ionic, covalent bonds or Van der Waal attractions to the wall of the vessel or some component thereof.

Alternately, as illustrated in FIGS. 16a–16c, the fluid 13 can be used for gene therapy on the vessel 11. In this embodiment, the fluid 13 can include a suitable viral vector 118 which is adapted to infect a cell 120 and replace, modulate, inhibit or enhance one of the cell genes 122 within the cell 120. For example, the fluid 13 could include a retroviral, adenoviral vectors or Adenovirus Associated Vectors (AAV) carrying the appropriate DNA payload for appropriate gene switching. Alternately, for example, naked DNA or polycation-condensed DNA could be utilized for gene therapy. The present invention allows for the use of fluids 13 which genetically alter the treatment area 54 of the vessel 11 without effecting the rest of the body.

Still other fluids 13 which could be utilized with the present invention include antibodies such as receptor site monoclonal antibodies, a toxic agent such as saponin, a genetic material such as DNA, a cellular material such as endothelial cells and/or medicaments such as heparin. The examples provided herein are merely examples of fluids 13 which may be useful with the present invention. Those skilled in the art will recognize that additional fluids 13 will be developed as medical technology improves. Additionally, those skilled in the art will recognize that the present invention can be utilized for application other than the inhibiting restenosis. For example, with extended dispensers 20, the present invention could deliver fluids 13 from the vessel 13 to specific organs.

OPERATION

An example of the operation of the balloon 16 version of the expanding member 15 can best be visualized with initial reference to FIGS. 1–3. First, the guidewire 38 is positioned into the vessel 11 of the patient 12. This is done to establish a mechanical pathway through the vessel 11 to the treatment area 54 where the fluid 13 is to be released.

Next, the balloon 16, which is attached to the catheter 14, is moved over the guidewire 38 to the treatment area 54. The balloon 16 is at its first configuration during movement in the vessel 11. Once the balloon 16 is properly positioned proximate the treatment area 54, an inflator 56 is activated to inflate the balloon 16 to its second configuration. As shown in FIG. 2, the inflator 56 is connected to the proximal (extracorporeal) end of the device 10.

Referring back to FIG. 3, it will be appreciated that, as the balloon 16 is inflated, the expanding balloon 16 urges against the tubular sleeve 18 and causes the tubular sleeve 18 to likewise expand. Consequently, the dispensers 20 mounted on the tubular sleeve 18 move radially from the catheter 14 and embed into the treatment area 54. Further, the balloon 16 can be used to simultaneously dilate the vessel 11.

With the dispensers 20 embedded into the treatment area 54, the fluid pump 58 shown in FIG. 2 is activated to pump fluid 13 from the fluid source 60 into the fluid passageway 26. Importantly, this pumping action also causes any fluid 13 which has already been pumped into the fluid passageway 26 to be expelled through the fluid channels 48 of dispensers 20 and into the tissue of treatment area 54.

Alternatively, the fluid pump 58 could be activated prior to embedding the dispensers 20 into the vessel wall 11 and a valve 62 could be used to prevent the flow of fluid 13 until the dispensers 20 are embedded in the treatment area 54. The valve 62 can then be opened when the dispensers 20 penetrate into the treatment area 54 so that injection occurs substantially simultaneously with the embedding of the dispensers 20 in the treatment area 54. Alternately, the injection of the fluid 13 could happen after a time delay by waiting to open the valve 62 for at least about one second to about twenty seconds. Further, one or more fluids 13 can be released at different time intervals in the vessel wall 11.

After the fluid 13 from the fluid source 60 has been dispensed into the treatment area 54, the balloon 16 can be deflated to the first configuration by reversing the inflator 56. This action will cause the balloon 16 to collapse and withdraw the dispensers 20 from the treatment area 54. The entire device 10 can then be withdrawn from the patient 12 over the guidewire 38.

The embodiment shown in FIGS. 6 and 7 utilizes a plurality of individual, tubular channels 64. With this embodiment, it is possible to either maintain fluid communication with, or fluid isolation between, each tubular channel 64. For example, fluid communication between each tubular channel 64 can be established by fluidly connecting each tubular channel 64 together within one outer lumen 27 of the catheter 14 so that each tubular channel 64 is supplied fluid 13 from the same fluid pump 58. Alternatively, fluid isolation may be maintained between each tubular channel 64 by providing each tubular channel 64 with a corresponding and independent outer lumen 27 and establishing its own fluid connection to a corresponding and independent fluid pump 58. Consequently, it is possible to inject a variety of alternate fluids 13 simultaneously by using a plurality of tubular channels 64 which are each connected to a separate fluid pump 58.

While the particular device 10 for injecting fluid 13 into the treatment area 54 as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method for treating a wall of a vessel, the vessel having a vessel pH level, the method comprising the steps of:

providing a fluid having a fluid pH level which is different from the vessel pH level, at least a portion of the fluid precipitating at approximately the vessel pH level; and dispensing the fluid into the wall of the vessel to allow at least a portion of the fluid to approach the vessel pH level and precipitate.

2. The method of claim 1 wherein the step of providing a fluid includes providing a fluid including an active component which inhibits the proliferation of smooth tissue growth in the wall of the vessel.

3. The method of claim 1 wherein the step of providing a fluid includes providing a fluid which includes gold colloidal.

4. The method of claim 1 wherein the step of providing a fluid includes providing a fluid which includes a radiopharmaceutical precipitate.

5. The method of claim 1 wherein the step of providing a fluid includes providing a fluid which includes an inorganic precipitate.

6. The method of claim 1 wherein the step of providing a fluid includes providing a fluid which has a fluid pH level of less than approximately six pH.

7. The method of claim 1 wherein the step of providing a fluid includes providing a fluid which has a fluid pH level of greater than approximately eight pH.

8. The method of claim 1 wherein the step of providing a fluid includes providing a fluid including $^{99m}$Tc (Technetium 99).

9. The method of claim 1 wherein the step of providing a fluid includes providing a fluid which includes $^{32}$P (Phosphorous 32).

* * * * *